(12) United States Patent
Pokrovski et al.

(10) Patent No.: US 9,156,752 B2
(45) Date of Patent: Oct. 13, 2015

(54) HIGH PURITY E-1-CHLORO-3,3,3-TRIFLUOROPROPENE AND METHODS OF MAKING THE SAME

(75) Inventors: Konstantin A. Pokrovski, Orchard Park, NY (US); Rajiv Ratna Singh, Getzville, NY (US); Ian Shankland, Randolph, NJ (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 300 days.

(21) Appl. No.: 12/984,024

(22) Filed: Jan. 4, 2011

(65) Prior Publication Data

US 2012/0172636 A1 Jul. 5, 2012

(51) Int. Cl.
*C07C 21/18* (2006.01)
*C07C 17/20* (2006.01)
*C07C 17/25* (2006.01)

(52) U.S. Cl.
CPC ............ *C07C 17/206* (2013.01); *C07C 17/25* (2013.01); *C07B 2200/09* (2013.01)

(58) Field of Classification Search
CPC ...... C07C 17/206; C07C 17/25; C07C 19/10; C07C 21/18; C07B 2200/09
USPC .................................. 570/135, 155, 160
See application file for complete search history.

(56) References Cited

U.S. PATENT DOCUMENTS

| | | | |
|---|---|---|---|
| 5,710,352 A | 1/1998 | Tung | |
| 6,077,982 A * | 6/2000 | Yates et al. | 570/177 |
| 6,291,730 B1 * | 9/2001 | Baker et al. | 570/176 |
| 6,313,360 B1 | 11/2001 | Wilson et al. | |
| 6,403,847 B1 | 6/2002 | Nakada et al. | |
| 6,472,573 B1 | 10/2002 | Yamamoto et al. | |
| 6,552,238 B1 | 4/2003 | Mainz et al. | |
| 6,720,466 B2 | 4/2004 | Wilson et al. | |
| 6,844,475 B1 | 1/2005 | Tung et al. | |
| 7,265,082 B2 | 9/2007 | Pham et al. | |
| 2009/0030244 A1 | 1/2009 | Merkel et al. | |
| 2009/0062576 A1 | 3/2009 | Eicher et al. | |
| 2009/0105510 A1 | 4/2009 | Quan et al. | |
| 2009/0256110 A1 | 10/2009 | Merkel et al. | |
| 2010/0072415 A1 * | 3/2010 | Rao et al. | 252/67 |
| 2011/0201853 A1 * | 8/2011 | Tung et al. | 570/168 |

FOREIGN PATENT DOCUMENTS

| | | | | |
|---|---|---|---|---|
| JP | 10-67693 | * | 10/1998 | |
| WO | WO 97/07083 | * | 2/1997 | |
| WO | 2005014512 A2 | | 2/2005 | |
| WO | WO-2009137658 | * | 11/2009 | C09K 3/30 |
| WO | 2010059496 A1 | | 5/2010 | |
| WO | 2010062572 A2 | | 6/2010 | |

OTHER PUBLICATIONS

Machine translation of JP 10-67693 (1998) conducted on the Japanese Patent website AIPN on Feb. 6, 2014.*
International Search Report & Written Opinion dated Jun. 26, 2012 for International Application No. PCT/US2012/020035.

* cited by examiner

*Primary Examiner* — Yevegeny Valenrod
*Assistant Examiner* — Blaine G Doletski
(74) *Attorney, Agent, or Firm* — Bruce O. Bradford

(57) ABSTRACT

The present invention discloses high purity E-1-chloro-3,3,3-trifluoropropene (1233zd(E)) and methods to produce the same. More specifically, the present invention discloses the methods of making 1233zd(E) essentially free of toxic impurities (e.g. 2-chloro-3,3,3-trifluoropropene (1233xf), chlorotetrafluoro-propene (1224), and 3,3,3-trifluoropropyne). The present invention further provides methods for making high purity 1233zd(E) with concentration of 1233xf and 1224 at or below 200 parts per million (ppm) and 3,3,3-trifluoropropyne impurities at or below 20 ppm. Formation of 1233xf impurity can be avoided if pure 1,1,1,3,3-pentachloropropane is used as a starting material. It was also found that formation of 1233xf is avoided if a liquid phase manufacturing process is used.

28 Claims, No Drawings

HIGH PURITY E-1-CHLORO-3,3,3-TRIFLUOROPROPENE AND METHODS OF MAKING THE SAME

BACKGROUND OF THE INVENTION

The compound E-1-chloro-3,3,3-trifluoropropene (1233zd (E)) is a next generation liquid low global warming potential (LGWP) foam blowing agent. This compound has the following structure:

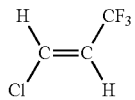

The compound 1233zd(E) is a known compound. It can be produced in a vapor phase reaction as taught in U.S. Pat. No. 5,710,352; or it can be produced in a liquid phase reaction as taught in U.S. Pat. No. 6,844,475. These patents are hereby incorporated herein by reference in their entirety.

The methods and compositions of the present invention are part of a continued search for the next generation of low global warming potential materials. Such materials must have low environmental impact, as measured by low global warming potential and/or low ozone depletion potential.

SUMMARY OF THE INVENTION

The present invention is directed to compositions and improved methods for the production of high purity 1233zd (E). More particularly, the present invention discloses methods of making 1233zd(E) essentially free of impurities, particularly the toxic impurities; 2-chloro-3,3,3-trifluoropropene (1233xf), and chlorotetrafluoropropene (1224), and the explosive impurity 3,3,3-trifluoropropyne; which can be present in other production methods. The presence of these and other impurities (e.g., 244bb and others) reduce the overall production yield of 1233zd(E) and regarding toxic or explosive impurities, such compounds can make the process more complex to operate safely.

For example, in the process comprising the fluorination of 240fa to form 1233zd(E), it has been found that even a small amount of certain impurities in the reactor feed, and in particular in the 240fa feed stock, can have a significant negative impact on the desirability of resulting reaction product stream and/or 1233zd(E) product, including particularly the purity of the resulting 1233zd(E).

The present invention further provides methods for making high purity 1233zd(E) in which the concentration of the impurities 1233xf and/or 1224 are at or below 200 parts per million (ppm) and the 3,3,3-trifluoropropyne impurity is at or below 20 ppm.

In one embodiment, it was discovered that the formation of the impurity 1233xf can be avoided if pure 1,1,1,3,3-pentachloropropane (240fa) is used as a starting material.

In another embodiment, it was discovered that the formation of the impurity 1233xf can be avoided if a liquid phase manufacturing process is used.

It has been found that one of the by-products in 1233zd(E) manufacturing process is 1233xf, which has the following structure:

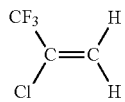

Due to the toxicity of 1233xf it is desired to reduce the concentration of 1233xf in the final product (1233zd(E)) to the levels at or below 200 parts per million (200 ppm). The presence of 1233xf in crude 1233zd(E) can result in significant yield losses during product purification due to the fact that 1233xf and 1233zd(E) are closely boiling compounds.

One embodiment of the present invention is a composition comprising 1233zd(E) at a purity of greater than about 99.6 percent by weight, and containing less than about 400 parts per million of 1233xf. Preferably, the composition contains less than about 300 parts per million of the impurity 1233xf. More preferably, the composition contains less than about 200 parts per million of 1233xf.

Another embodiment of the present invention is a composition comprising 1233zd(E) at a purity of greater than about 99.6 percent by weight, and containing less than about 50 parts per million of the impurity 3,3,3-trifluoropropyne. Preferably, the composition contains less than about 20 parts per million of 3,3,3-trifluoropropyne.

Yet another embodiment of the present invention is a composition comprising 1233zd(E) at a purity of greater than about 99.6 percent by weight, and containing less than about 400 parts per million of the impurity 1224. Preferably, the product contains less than about 200 parts per million of 1224.

Yet another embodiment of the present invention is a composition comprising 1233zd(E) at a purity of greater than about 99.6 percent by weight, and containing less than about 400 parts per million of the impurity 244bb. Preferably, the composition contains less than about 200 parts per million of 244bb.

Another embodiment of the present invention is the composition comprising 1233zd(E) at a purity of greater than about 99.6 percent by weight, and containing less than about 400 parts per million of 244fa. Preferably, the composition contains less than about 200 parts per million of 244fa.

Another embodiment of the present invention is a method for producing 1233zd(E) from 240fa comprising the steps of:
  (a) feeding at least one reactor feed stream containing 240fa to a least one fluorination reactor and
  (b) ensuring that said at least one feed stream contains not more than about 0.2% by weight of 240 db.

Here it must be noted that the feed stream may also include one or more dehydrochlorination derivatives of 240fa and/or 240 db. For example, dehydrochlorination of 240fa gives 1,1,3,3-tetrachloropropene and 1,3,3,3-tetrachloropropene. Derivatives of 240 db are 1,1,2,3-tetrachloropropene and 2,3,3,3-tetrachloropropene. These compounds may be present in the reaction streams, and use of the designations 240fa and/or 240 db herein, unless otherwise specified, is intended to include the mixtures of those compounds with one or more of their respective dehydrochlorination derivatives.

In this method, the 240fa feed stream preferably contains at least about 99.8% by weight of 240fa. Preferably, the 240fa feed stream contains not more than about 0.1% by weight of 240 db. More preferably, the 240fa feed stream contains not more than about 0.08% of 240 db.

DETAILED DESCRIPTION OF THE INVENTION

As described above, the present invention discloses high purity 1233zd(E) and methods to produce the same. More specifically, the present invention discloses the methods of making 1233zd(E) essentially free of toxic and other yield affecting impurities that are formed during various processing steps of the starting materials and/or the processing reactions.

The production of 1233xf via fluorination of 240 db with HF is disclosed in US Patent Publication No. 20090030244. U.S. Pat. Nos. 6,844,475 and 5,710,352 disclose processes for producing 1233zd(E) by catalytic fluorination of 240fa with anhydrous hydrogen fluoride (HF). While these patents disclose processes having relatively high conversion levels, the present inventors have come to appreciate that these reactions can be improved as taught herein. These documents are hereby incorporated herein by reference.

In particular embodiments, the present inventors have found that even small amounts of 240 db in the reactor feed has a surprising and unexpectedly negative impact on the purity of the reaction product, and in particular the resulting 1233zd(E) product. It has been found that 240 db present as an impurity in the 240fa starting material, can be converted to the toxic compound, 1233xf under normal reaction conditions. This invention discloses a safe level (at or below 200 ppm) of 1233xf impurity in the 1233zd(E) product and methods to eliminate the impurity from the final product. This process is similar to the process described in U.S. Pat. No. 6,274,779, which is hereby incorporated herein by reference.

In preferred embodiments, the toxic impurity 1233xf is removed to below 200 ppm, from the reaction that generates the desired compound, 1233zd(E). In one especially preferred embodiment, Table I below shows the purity profile for product grade 1233zd(E).

TABLE I

| Purity Profile | | |
| --- | --- | --- |
| Component | wt % | Ppm |
| trans-1233zd (1233zd(E)) | 99.6080% | |
| 3,3,3,-trifluoropropyne | 0.0020% | 20 |
| trans-1234ze (1234ze(E)) | 0.1000% | 1000 |
| cis-1234ze (1234ze(Z)) | 0.1000% | 1000 |
| 245fa | 0.1000% | 1000 |
| 1233xf | 0.0200% | 200 |
| 244bb | 0.0200% | 200 |
| 1224 isomer | 0.0200% | 200 |
| cis-1233zd (1233zd(Z)) | 0.0500% | 500 |
| 244fa | 0.0200% | 200 |

Sources of Impurities (A) The 1233xf and 244bb impurities can be formed from the 240 db impurity, as follows; 240 db+3HF→1233xf+4HCl. The 244bb impurity is the product of HF addition to 1233xf. These impurities can also be formed from derivatives of 240 db.

(B) The impurity 3,3,3-trifluoropropyne ($CF_3$≡CCH) can be formed from deep dehydrohalogenation of the reaction products/by-products; if HF or HCl is removed from $CF_3$—CX=CYH (or 2 molecules of HF/HCl are removed from saturated $CF_3$—CXY—CHVZ) where V, X, Y, Z are H, F, or Cl).

(C) The impurity 1224 isomer can be formed from one of the impurities in crude 240fa. Also the impurity 1224 isomer may be formed via interaction of one or more of the reactions products with HCl.

Accordingly, one preferred aspect of the invention provides methods for producing 1233zd(E), and preferably high purity 1233zd(E) product, from 240fa comprising the steps of:

(a) feeding at least one reactor feed stream containing 240fa to a least one fluorination reactor and
(b) ensuring that said at least one feed stream contains not more than about 0.2% by weight, even more preferably not more than about 0.1% by weight, even more preferably not more than about 0.08% of 240 db impurity.

Another preferred aspect of the invention provides method of producing high purity 1233zd(E) from 240fa via liquid phase fluorination reaction that contrary to vapor phase fluorination reaction does not result in the formation of 1233xf impurity.

In certain preferred embodiments, the methods comprise providing a raw feed stock comprising at least about 99.8% by weight of 240fa and a minority of 240 db.

In certain preferred embodiments, the methods of the present invention are carried out under conditions effective to produce a final product comprising a majority of 1233zd(E), containing from 0 to about 200 ppm of 1233xf, from 0 to about 20 ppm of 3,3,3-trifluoropropyne, and from 0 to about 200 ppm 1224, which conditions optionally but preferably include distilling said reaction product.

Separating raw 240fa feed stock from 240 db impurity by means of distillation or any other method known in the art, and fluorinating said purified 240fa feed stock with less than 0.2 wt % of 240 db impurity with anhydrous HF into 1233zd(E) in the presence of a catalyst in vapor phase and preferably in the presence of a catalyst in liquid phase, and separating the crude 1233zd(E) reaction product from the impurities using liquid-liquid extraction, gas-liquid extraction, solid absorbent, distillation utilizing one or more distillation columns, or other means known in the art to have a final product concentration of 1233xf that is below 300 ppm, preferably below 100 ppm, and more preferably below 50 ppm, 1224 that is below 300 ppm, preferably below 100 ppm, and more preferably below 50 ppm, and a final product concentration of 3,3,3-trifluoropropyne that is below 50 ppm, preferably below 20 ppm.

Separation of 240fa from 240 db Impurity

In certain embodiments, the content of 240 db impurity in the 240fa raw feed may be reduced by any means known in the art, such as extraction and preferably distillation. Although it is contemplated that a wide range of separation conditions can be used in accordance with the present invention, it is preferred in certain embodiments that the 240fa raw materials are distilled by passing through a standard distillation column and/or packed tower, or the like at atmospheric pressure, or preferably sub-atmospheric pressure. Preferably the pressure is less than about 16 psia, more preferably less than about 12 psia, and most preferably less than 10 psia. The pressure of the distillation column inherently determines the distillation operating temperature for a given degree of separation. The 240fa may be recovered as distillate by operating the distillation column at the temperatures below 190° C., preferably below 100° C., more preferably below 80° C. Single or multiple distillation columns may be used. In certain preferred embodiments, the purity of 240fa after distillation is at least about 99.8 wt %.

Fluorination of 240fa to Produce Crude 1233zd(E) Product

Fluorination of 240fa can be carried out in vapor phase or liquid phase process using anhydrous HF. The fluorination of 240fa can be facilitated by the use of a catalyst.

Vapor Phase Fluorination of 240fa.

The manufacturing process for the vapor phase fluorination of 240fa consists of the following 3 major unit operations:

(1) Fluorination reaction (continuous mode) using HF;
(2) Separation and purification of byproduct HCl; and
(3) Separation of excess HF and recycle back to step (1).

Catalytic fluorination of 1,1,1,3,3-pentachloropropane

Reactor

This reaction will be conducted in a vapor phase reactor. Preferably the reactor is constructed from materials which are resistant to the corrosive effects of the HF and catalyst, such as Hastelloy-C, Inconel, Monel, Incolloy. Such vapor phase fluorination reactors are well known in the art.

240fa and HF are vaporized and simultaneously fed to into a vapor phase reactor. The reaction temperature is from about 250° C. to 450° C. and at from about 0 to 125 psig pressure. The mole ratio of HF to 240fa is greater than or equal to 3:1, preferably between 3:1 and 20:1, more preferably between 4:1 and 12:1, and most preferably between 5:1 and 10:1. The reactor effluent consisting of partially fluorinated intermediates and by-products, overfluorinated by-products, HF, 1233zd(E+Z), and HCl, then available for purification.

Catalyst

Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures. Catalysts can be supported or in bulk. Combinations of catalysts suitable for the present invention nonexclusively include $Cr_2O_3$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Additional fluorination catalysts that can be used include $FeCl_3/C$, $SnCl_4/C$, $TaCl_5/C$, $SbCl_3/C$, $AlCl_3/C$, and $Al_3/C$. The support for the metal halides listed can also be alumina or fluorinated alumina. All of the listed catalysts are partially or totally fluorinated by anhydrous HF.

Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

The preferred catalyst in R-1 is fluorinated chrome oxide. The reactor effluent consisting of partially fluorinated intermediates and by-products, overfluorinated by-products, HF, 1233zd(E+Z), and HCl, then enters HCl recovery column.

Removal of HCl

The HCl formed continuously during the reaction is removed from the reactor due to its volatile nature, and flows through the attached distillation column without condensing. The material can then be purified and collected for sale (or further purification) by using a low-temperature HCl distillation column. High purity HCl is isolated and can be absorbed in de-ionized water for sale as concentrated HCl.

Separation and Recycle of Excess HF

The bottoms (or heavy) stream from the HCl column (2) that contains crude product mixture of 1233zd(E) and about 30-60 wt % HF is fed to a sulfuric extractor or phase separator for removal of HF from this mixture. HF is either dissolved in the sulfuric acid or phase separated from the organic mixture. HF is desorbed from the sulfuric acid/HF mixture by stripping distillation and recycled back to the reactor. In case a phase separator is used, HF is phase-separated and recycled back to the reactor. The organic mixture either from the overhead of the sulfuric acid extractor or from the bottom layer of the phase separator may require treatment (scrubbing or adsorption) to remove traces of HF before it is available for further purification.

Reactor and Stripping Column

The arrangement and operation of the reactor and stripping column is particularly important in achieving a high yield of 1233zd(E). In a preferred embodiment, the reaction is conducted in an agitated, temperature-controlled reactor containing the liquid fluorination catalyst. One or more feeds comprising hydrogen fluoride and 240fa enter the reactor where they contact each other and the catalyst in a liquid phase. The resulting reaction produces a gas phase product comprising 1233zd(E) as well as various other by-products including HCl and possibly 1233zd(Z).

The gas phase product leaves the liquid phase reactor and enters an integrated distillation column (operating in stripping mode) which permits the desired product to leave, along with by-product HCl, traces of light organics (principally 1234ze (E+Z)), and sufficient anhydrous hydrogen fluoride (AHF) to form the azeotropes, while retaining the bulk of the HF, plus under-fluorinated and dimerized organics, plus fluorination catalyst entrained in the gas stream.

Once the catalyst has been prepared, the reaction can be initiated immediately upon heating to the desired reaction temperature. The flow of HF needed for the catalyst preparation can be resumed, and addition of the hydrochlorocarbon (1,1,1,3,3-pentachloropropane) can be started immediately to cause continuous reaction.

Alternatively, a large amount of the same hydrochlorocarbon can be added at one time (batch charge), and then HF can be added gradually to the reactor (a semi-batch operation). Alternatively, a large amount of HF can be added at one time batch charge, and then the same hydrochlorocarbon can be added gradually to the reactor (a semi-batch operation). Proper temperature control of the coolant and sufficient reflux action are desirable for optimum operation of stripping column to be effective.

General operating conditions which have been found to work well for the reaction and stripping are: Operating pressure of from about 80 to 140 psig are maintained by a control valve on the exiting flow from the stripper column. Reactor temperatures of from about 85° to 120° C. are primarily supplied by steam flow into the reactor jacket. Cooling to temperatures in the range of from about −40° C. to 25° C. is conducted by application of brine cooling to the heat exchanger on top of the stripper column to induce reflux. The temperature in the center portion of the stripper is typically from about 10° to 40° C. below that in the reactor. Additional heat input is provided by superheating the HF vapor feed with high-pressure steam to from about 120° to 150° C. The feed rate of HF is sufficient to maintain the desired reactor and stripper conditions.

Removal of HCl

The HCl formed continuously during the reaction is removed from the reactor due to its volatile nature, and flows through the attached distillation column without condensing. The material can then be purified and collected for sale (or further purification) by using a low-temperature HCl distillation column. High purity HCl is isolated and can be absorbed in de-ionized water for sale as concentrated HCl.

Separation and Recycle of Excess HF

The bottoms (or heavy) stream from the HCl removal column (3) that contains crude product mixture of 1233zd(E) and HF (in some embodiments about 30 wt %) is fed to a sulfuric extractor or a phase separator for removal of HF from this mixture. HF is either dissolved in the sulfuric acid or phase separated from the organic mixture. For embodiments utilizing a sulfuric acid adsorption system, the HF is then desorbed from the sulfuric acid/HF mixture by stripping distillation and recycled back to the reactor. For embodiments utilizing a phase separator, HF is phase-separated and recycled back to the reactor. The organic mixture either from the overhead of the sulfuric acid extractor or from the bottom layer of the phase separator may require treatment (scrubbing or adsorption) to remove traces of HF before it becomes available for further purification.

Purification of 1233zd(E)

The purification of the 1233zd(E) product can be performed by means of liquid-liquid extraction, gas-liquid extraction, using solid absorbent, or preferably by distillation utilizing one or more distillation columns in a batch or continuous mode.

Purification of 1233zd(E) product by distillation. In one non limiting embodiment two distillation columns are used in continuous mode to produce high purity 1233zd(E) product. The crude 1233zd(E) free of HF and HCl by-product is fed into the first distillation column (lights column). A stream exiting the top of the lights column consists mainly of reaction by-products that have boiling points lower than that of 1233zd(E) such as 3,3,3-trifluoropropyne, 1233xf, 1224, and the like.

The stream exiting the bottom of lights column consisting mainly of 1233zd(E+Z), heavier by-products, and with concentration of 1233xf at or below 200 ppm, concentration of 1224 at or below 200 ppm, and concentration of 3,3,3-trifluoropropyne at or below 20 ppm is fed to product recovery distillation column. Product grade 1233zd(E) with concentration of 1233xf at or below 200 ppm, concentration of 1224 at or below 200 ppm, and concentration of 3,3,3-trifluoropropyne at or below 20 ppm exits the top of the column to product storage. The product column bottoms consist mainly of 1233zd(Z) and reaction by-products with boiling points higher than that of 1233zd(E). This bottoms stream is collected for later use or disposal.

Example 1

This example illustrates the continuous vapor phase fluorination reaction of 240fa with hydrogen fluoride to produce 1233zd, as per the reaction:

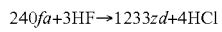

The fluorination catalyst for the experiment was fluorinated $Cr_2O_3$. The 240fa feed material contained about 0.14 GC Area % of 240 db impurity.

A continuous vapor phase fluorination reaction system consisting of $N_2$, HF, and organic feed systems, feed vaporizer, superheater was used with a two inch inner diameter Monel reactor, acid scrubber, drier, and product collection system to study the reaction. The reactor was loaded with 2135 grams of pretreated $Cr_2O_3$ catalyst which equates to about 1.44 liters of catalyst. The reactor was then heated to a reaction temperature of about 275° C. with a $N_2$ purge going over the catalyst after the reactor had been installed in a constant temperature sand bath. The reactor was at about 2 psig of pressure.

HF feed was introduced to the reactor (via the vaporizer and superheater) as a co-feed with the $N_2$ for 15 minutes when the $N_2$ flow was stopped. The HF flow rate was adjusted to 1.0 lb/hr and then the 240fa feed was started to the reactor (via the vaporizer and superheater). The feed rate of the 240fa was kept steady at about 1.2 lb/hr and HF feed was kept steady at 1.0 lb/hr to maintain about a 9 to 1 mole ratio of HF to 240fa.

Once the reaction started the catalyst bed temperature was adjusted to about 328° to 332° C.

The average composition of the material at the exit from reactor was about 81.35 GC area % 1233zd(E), 9.18 GC area % 1233zd(Z), 3.65 GC area % 1234ze(E), 2.83 GC area % 245fa, 1.46 GC area % 1234ze(Z), 0.18 GC area % 1233xf, 0.05 GC area % 3,3,3-trifluoropropyne, and about 1.3 GC area % others including chlorotetrafluoro-propene. During about 200 hours on stream the position of the hot spot inside catalyst bed moved from the inlet to the exit section of the reactor indicating partial deactivation of the catalyst. The conversion of 240fa was about 100% throughout the run.

Example 2

This example is similar to the Example 1 and illustrates the continuous vapor phase fluorination reaction of 240fa with hydrogen fluoride to produce 1233zd according to the reaction:

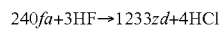

The fluorination catalyst for the experiment was fluorinated $Cr_2O_3$. The 240fa feed material contained about 0.07 GC Area % of 240 db impurity.

A continuous vapor phase fluorination reaction system consisting of $N_2$, HF, organic feed systems, feed vaporizer, and a superheater. A two-inch inner diameter Monel reactor, acid scrubber, drier, and product collection system was used to study the reaction. The reactor was loaded with 2135 grams of pretreated $Cr_2O_3$ catalyst which equates to about 1.44 liters of catalyst. The reactor was then heated to a reaction temperature of about 275° C. with a $N_2$ purge going over the catalyst after the reactor had been installed in a constant temperature sand bath. The reactor was at about 2 psig of pressure.

HF feed was introduced to the reactor (via the vaporizer and superheater) as a co-feed with the $N_2$ for 15 minutes when the $N_2$ flow was stopped. The HF flow rate was adjusted to about 1.3 lb/hr and then the 240fa feed was started to the reactor (via the vaporizer and superheater). The feed rate of the 240fa was kept steady at about 2.1 lb/hr and HF feed was kept steady at about 1.3 lb/hr to maintain about a 6.7 to 1 mole ratio of HF to 240fa. Once the reaction started the catalyst bed temperature was adjusted to from about 329° to 335° C.

The average composition of the material at the exit from reactor was about 83.77 GC area % 1233zd(E), 9.02 GC area % 1233zd(Z), 1.51 GC area % 1234ze(E), 2.62 GC area % 245fa, 0.44 GC area % 1234ze(Z), 0.08 GC area % 1233xf, 0.07 GC area % 3,3,3-trifluoropropyne, and about 2.5 GC area % others including chlorotetrafluoro-propene. During about 200 hours on stream the position of the hot spot inside catalyst bed moved from the inlet to the exit section of the reactor indicating partial deactivation of the catalyst. The conversion of 240fa was about 100% throughout the run.

Example 3

This example illustrates the semi-batch reaction where HF is continuously fed into a charge of titanium tetrachloride catalyst and 240fa. The 240fa starting material contained about 0.14 GC Area % of 240 db impurity.

A clean, empty 10-gallon jacketed, agitated reactor of Hastelloy C construction was prepared. This reactor was connected to a two-inch inner diameter by 8 foot long vertical, PTFE-lined pipe containing packing material (catalyst stripper column), which was in turn connected to an overhead heat exchanger. The heat exchanger was supplied with −40° C. brine circulation on the shell side.

Vapors exiting this catalyst stripper were processed through a caustic scrubber, in which temperature-controlled dilute potassium hydroxide aqueous solution was circulated. Acid free reaction products exiting this caustic scrubber were collected in a weighed, chilled (−40° C.) cylinder referred to as the product collection cylinder, followed by a smaller cylinder in series chilled in a dry ice bath.

For this experiment, 14 lbs. of anhydrous HF were fed into the reactor to assure catalyst fluorination. Next, 1.5 lbs. of $TiCl_4$ were added as a catalyst, followed immediately by 50 lbs. of 240fa. Additional HF was then fed continuously. The GC analysis of the crude material collected during the run was as follows; 86.4% 1233zd(E); 5.5% G-244fa; 3.1% 1234ze (E); 1.5% 1233zd(Z); 1.1% 1234ze(Z); 1.1% dimer; and 0.2% trifluoropropyne.

Example 4

This example illustrates the purification of the target product 1233zd(E). A distillation column was charged with 118.9 lb of the crude 1233zd product. The composition of the crude mixture is presented in Table 2.

TABLE 2

Composition of crude 1233zd product charged in to the distillation column.

| Component | Concentration (GC %) |
|---|---|
| $CF_3CCH$ | 3.74 |
| 1234ze(E) | 7.65 |
| 1234ze(Z) | 1.06 |
| 245fa | 1.75 |
| 1233xf | 0.11 |
| 1233zd(E) | 81.38 |
| 1233zd(Z) | 4.08 |
| Others | 0.23 |

The distillation column consisted of a 10 gallon reboiler, a two-inch inner diameter by 10 feet long column packed with propack distillation packing, and a shell and tube condenser. The column had about 30 theoretical plates. The distillation column was equipped with temperature, pressure, and differential pressure transmitters. The distillation was run at a pressure of from about 40 to 50 psig during lights cut and at pressure of about 30 psig during main, 1233zd(E) cut. The distillate was sampled and analyzed by GC at regular intervals. Two separate cuts were collected: lights cut and main, essentially pure 1233zd(E) cut. The heavies cut was discharged from the reboiler. The recovery of essentially pure 1233zd(E) was about 76%. The compositions and weights of three cuts are listed in Table 3.

TABLE 3

Composition of the distillation cuts collected during the distillation described in the Example 4.

| Component | 1233zd(E)cut 73.8 lb Concentration (GC %) | LIGHTS 38.3 lb Concentration (GC %) | BOTTOMS 6.8 lb Concentration (GC %) |
|---|---|---|---|
| $CF_3CCH$ | 0.0015 | 11.6 | — |
| 1234ze(E) | 0.0060 | 23.75 | — |
| 1234ze(Z) | 0.0063 | 3.3 | — |
| 245fa | 0.0084 | 5.44 | — |
| 1233xf | 0.0020 | 0.35 | — |
| 1233zd(E) | 99.97 | 55.29 | 26.18 |
| 1233zd(Z) | 0.0008 | — | 71.29 |
| Others | 0.005 | 0.27 | 2.53 |

These processes use 1,1,1,3,3-pentachloropropane and HF as starting materials. Often 1,1,1,3,3-pentachloropropane contains 1,1,1,2,3-pentachloropropane as an impurity resulting in the formation of 2-chloro-3,3,3-trifluoropropene (1233xf) by-product. The 1233xf impurity can be separated from 1233zd(E) by conventional distillation.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An impure product consisting essentially of a mixture of E-1-chloro-3,3,3-trifluoropropene (1233zd(E)) and 2-chloro-3,3,3-trifluoropropene (1233xf);
   wherein the impure product contains greater than zero and less than about 400 parts per million of 2-chloro-3,3,3-trifluoropropene (1233xf) and has a 1233zd(E) purity of greater than about 99.6 percent by weight.

2. The impure product of claim 1, which contains greater than zero and less than about 300 parts per million of 2-chloro-3,3,3-trifluoropropene (1233xf).

3. The impure product of claim 1, which contains greater than zero and less than about 200 parts per million of 2-chloro-3,3,3-trifluoropropene (1233xf).

4. An impure product consisting essentially of a mixture of E-1-chloro-3,3,3-trifluoropropene (1233zd(E)) and 3,3,3-trifluoropropyne;
   wherein the impure product contains greater than zero and less than about 50 parts per million of 3,3,3-trifluoropropyne; and
   wherein the impure product has a 1233zd(E) purity of greater than about 99.6 percent by weight.

5. The impure product of claim 4, which contains greater than zero and less than about 20 parts per million of 3,3,3-trifluoropropyne.

6. An impure product consisting essentially of a mixture of E-1-chloro-3,3,3-trifluoropropene (1233zd(E)) and chlorotetrafluoropropene (1224);
   wherein the impure product contains greater than zero and less than about 400 parts per million of chlorotetrafluoropropene (1224) and
   wherein the impure product has a 1233zd(E) purity of greater than about 99.6 percent by weight.

7. The impure product of claim 6, which contains greater than zero and less than about 300 parts per million of chlorotetrafluoropropene (1224).

8. The impure product of claim 6, which contains greater than zero and less than about 200 parts per million of chlorotetrafluoropropene (1224).

9. An impure product consisting essentially of a mixture of E-1-chloro-3,3,3-trifluoropropene (1233zd(E)) and 2-chloro-2,1,1,1-tetrafluoropropane (244bb);
   wherein the impure product contains greater than zero and less than about 400 parts per million of 2-chloro-2,1,1,1-tetrafluoropropane (244bb), and
   wherein the impure product has a 1233zd(E) purity of greater than about 99.6 percent by weight.

10. The impure product of claim 9, which contains greater than zero and less than about 300 parts per million of 2-chloro-2,1,1,1-tetrafluoropropane (244bb).

11. The impure product of claim 10, which contains greater than zero and less than about 200 parts per million of 2-chloro-2,1,1,1-tetrafluoropropane (244bb).

12. An impure product consisting essentially of a mixture of E-1-chloro-3,3,3-trifluoropropene (1233zd(E)) and 3-chloro-3,1,1,1-tetrafluoropropane (244fa);
    wherein the impure product contains greater than zero and less than about 400 parts per million of 3-chloro-3,1,1,1-tetrafluoropropane (244fa); and
    wherein the impure product has a 1233zd(E) purity of greater than about 99.6 percent by weight.

13. The impure product of claim 12, which contains greater than zero and less than about 300 parts per million of 3-chloro-3,1,1,1-tetrafluoropropane (244fa).

14. The impure product of claim 12, which contains greater than zero and less than about 200 parts per million of 3-chloro-3,1,1,1-tetrafluoropropane (244fa).

15. The impure product composition of claim 12, further containing 2-chloro-3,3,3-trifluoropropene (1233xf), at an amount greater than zero and less than 400 parts per million.

16. The impure product of claim 15, which contains greater than zero and less than about 300 parts per million of 2-chloro-3,3,3-trifluoropropene (1233xf).

17. The impure product of claim 15, which contains greater than zero and less than about 200 parts per million of 2-chloro-3,3,3-trifluoropropene (1233xf).

18. An impure composition consisting of a mixture of at least 99.6 percent by weight E-1-chloro-3,3,3-trifluoropropene (1233zd(E)), and 3,3,3-trifluoropropyne;
    wherein the amount of 3,3,3-trifluoropropyne in the impure composition is greater than zero and less than 50 parts per million.

19. The impure composition of claim 18, which contains greater than zero and less than about 20 parts per million of 3,3,3-trifluoropropyne.

20. An impure composition consisting of a mixture of at least 99.6 percent by weight E-1-chloro-3,3,3-trifluoropropene (1233zd(E)), and chlorotetrafluoropropene (1224), wherein the amount of 1224 in the impure composition is greater than zero and less than 400 parts per million.

21. The impure composition of claim 20, which contains greater than zero and less than about 300 parts per million of chlorotetrafluoropropene (1224).

22. The impure composition of claim 20, which contains greater than zero and less than about 200 parts per million of chlorotetrafluoro-propene (1224).

23. An impure composition consisting of a mixture of at least 99.6 percent by weight E-1-chloro-3,3,3-trifluoropropene (1233zd(E)), and 2-chloro-2,1,1,1-tetrafluoro-propane (244bb);
    wherein the amount of 244bb in the impure composition is greater than zero and less than 400 parts per million.

24. The impure composition of claim 23, which contains greater than zero and less than about 300 parts per million of 2-chloro-2,1,1,1-tetrafluoropropane (244bb).

25. The impure composition of claim 23, which contains greater than zero and less than about 200 parts per million of 2-chloro-2,1,1,1-tetrafluoropropane (244bb).

26. A impure composition consisting of a mixture of at least 99.6 percent by weight E-1-chloro-3,3,3-trifluoropropene (1233zd(E)), and 3-chloro-3,1,1,1-tetrafluoropropane (244fa);
    wherein the amount of 244fa in the impure composition is greater than zero and less than 400 parts per million.

27. The impure composition of claim 26, which contains greater than zero and less than about 300 parts per million of 3-chloro-3,1,1,1-tetrafluoropropane (244fa).

28. The impure composition of claim 26, which contains greater than zero and less than about 200 parts per million of 3-chloro-3,1,1,1-tetrafluoropropane (244fa).

* * * * *